(12) United States Patent
Kadamus et al.

(10) Patent No.: US 10,561,407 B2
(45) Date of Patent: Feb. 18, 2020

(54) APPARATUSES AND METHODS FOR ENDOSCOPIC TOOL JOINTS

(71) Applicant: HOYA Corporation, Tokyo (JP)

(72) Inventors: Christopher Kadamus, West Roxbury, MA (US); Robb Morse Gavalis, Westborough, MA (US); Azadeh Khanicheh, Somerville, MA (US); Isaac Ostrovsky, Wellesley, MA (US); Hrishikesh Vishvas Deo, Brooklyn, NY (US); James S. Pelletier, Boston, MA (US)

(73) Assignee: HOYA CORPORATION, Tokyo (JP)

( * ) Notice: Subject to any disclaimer, the term of this patent is extended or adjusted under 35 U.S.C. 154(b) by 281 days.

(21) Appl. No.: 15/587,756

(22) Filed: May 5, 2017

(65) Prior Publication Data

US 2018/0317896 A1 Nov. 8, 2018

(51) Int. Cl.
*A61B 17/00* (2006.01)
*A61B 10/04* (2006.01)

(52) U.S. Cl.
CPC ........ *A61B 17/00234* (2013.01); *A61B 10/04* (2013.01); *A61B 2010/045* (2013.01); *A61B 2017/00477* (2013.01); *A61B 2017/00526* (2013.01)

(58) Field of Classification Search
CPC .............. A61B 17/00234; A61B 10/04; A61B 2010/045; A61B 2017/00477; A61B 2017/00526
USPC ............................................................ 606/1
See application file for complete search history.

(56) References Cited

U.S. PATENT DOCUMENTS

| | | | |
|---|---|---|---|
| 4,869,259 | A | 9/1989 | Elkins |
| 5,201,314 | A | 4/1993 | Bosley et al. |
| 5,573,008 | A | 11/1996 | Robinson et al. |
| 5,766,135 | A | 6/1998 | Terwilliger |
| 5,769,795 | A | 6/1998 | Terwilliger |
| 6,228,039 | B1 | 5/2001 | Binmoeller |
| 6,258,064 | B1 | 7/2001 | Smith et al. |
| 6,585,694 | B1 | 7/2003 | Smith et al. |

(Continued)

OTHER PUBLICATIONS

International Search Report and Written Opinion for International Application No. PCT/IB2018/000610 filed May 4, 2018, dated Oct. 9, 2018, 13 pages.

*Primary Examiner* — Carl H Layno
*Assistant Examiner* — Erin M Piateski
(74) *Attorney, Agent, or Firm* — Finnegan, Henderson, Farabow, Garrett & Dunner, L.L.P.

(57) ABSTRACT

Embodiments of the present disclosure are directed to apparatuses, devices, and methods for secure connections between tubular structures. In one implementation, a first tube constructed of nitinol may have windows formed on an end thereof. A second tube constructed of stainless steel tube may be inserted within the first tube, and the windows may be filled with adhesive or solder. The adhesive or solder may bond with the first tube, forming connection pins which secure the tubes together. In some embodiments, the connected tubes may form an endoscopic needle. The nitinol portion of the needle may be sufficiently flexible for positioning within the bending section of an endoscope without deformation. The stainless steel portion of the needle may render the needle significantly less expensive than prior needles constructed solely of nitinol.

17 Claims, 6 Drawing Sheets

(56) References Cited

U.S. PATENT DOCUMENTS

| | | |
|---|---|---|
| 6,623,437 B2 | 9/2003 | Hinchliffe et al. |
| 6,656,132 B1 | 12/2003 | Ouchi |
| 6,976,955 B2 | 12/2005 | Hardin et al. |
| 7,641,638 B2 | 1/2010 | Waxman et al. |
| 7,722,549 B2 | 5/2010 | Nakao |
| 7,828,746 B2 | 11/2010 | Teague |
| D657,461 S | 4/2012 | Schembre et al. |
| 8,226,575 B2 | 7/2012 | Levy |
| 8,328,837 B2 | 12/2012 | Binmoeller |
| 8,369,935 B2 | 2/2013 | Ryan |
| 8,460,176 B2 | 6/2013 | McGrath |
| 8,506,503 B2 | 8/2013 | Fritscher-Ravens et al. |
| D690,009 S | 9/2013 | Schembre et al. |
| 8,597,242 B2 | 12/2013 | Fink |
| 8,608,701 B2 | 12/2013 | Tonomura |
| 8,622,994 B2 | 1/2014 | Wendlandt et al. |
| 8,628,475 B2 | 1/2014 | Wang |
| 8,656,928 B2 | 2/2014 | Carlson et al. |
| 8,657,749 B2 | 2/2014 | Sato |
| 8,663,168 B2 | 3/2014 | Chin et al. |
| 8,708,931 B2 | 4/2014 | Takeuchi et al. |
| 8,920,337 B2 | 12/2014 | Weisman et al. |
| 8,968,210 B2 | 3/2015 | Mugan et al. |
| 9,033,865 B2 | 5/2015 | Suda |
| 9,125,638 B2 | 9/2015 | Chin et al. |
| 9,144,459 B2 | 9/2015 | Surti et al. |
| 9,186,128 B2 | 11/2015 | Mugan et al. |
| 9,198,686 B2 | 12/2015 | Motai et al. |
| 9,216,258 B2 | 12/2015 | Devereux et al. |
| 9,282,948 B2 | 3/2016 | Melchiorri et al. |
| 9,289,231 B2 | 3/2016 | Clancy |
| 9,332,973 B2 | 5/2016 | McWeeney et al. |
| 9,351,710 B2 | 5/2016 | McGhie et al. |
| 9,351,711 B2 | 5/2016 | Weisman et al. |
| 9,386,963 B2 | 7/2016 | Ryan et al. |
| 9,456,806 B2 | 10/2016 | Chudzik et al. |
| 9,463,000 B2 | 10/2016 | Weisman et al. |
| 9,521,993 B2 | 12/2016 | Ryan |
| 2004/0260199 A1 | 12/2004 | Hardia, Jr. et al. |
| 2006/0259118 A1* | 11/2006 | Pal ............... A61F 2/95 623/1.11 |
| 2006/0264828 A1* | 11/2006 | Woehr ............ A61M 5/3273 604/110 |
| 2009/0056199 A1* | 3/2009 | Reed ............. B29C 65/606 43/131 |
| 2010/0121218 A1* | 5/2010 | Mugan ........... A61B 10/0283 600/567 |
| 2010/0298761 A1* | 11/2010 | Staal ............. A61N 1/327 604/20 |
| 2012/0226101 A1 | 9/2012 | Tinkham et al. |
| 2013/0053822 A1* | 2/2013 | Fischell ......... A61M 25/0084 604/510 |
| 2014/0257136 A1 | 9/2014 | Leahy et al. |
| 2015/0066089 A1* | 3/2015 | Nelson ........... A61B 17/7083 606/265 |
| 2015/0265258 A1 | 9/2015 | Toomey et al. |
| 2016/0331358 A1 | 11/2016 | Gordon |
| 2016/0361047 A1* | 12/2016 | Rohl ............. A61B 10/04 |

\* cited by examiner

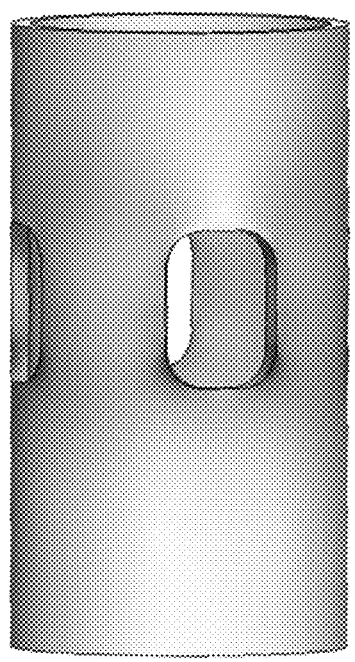 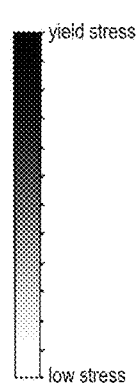 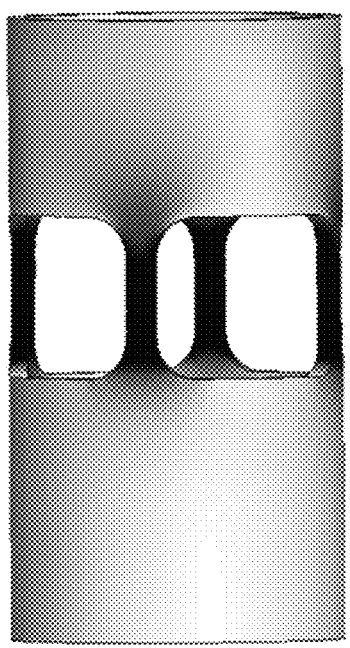 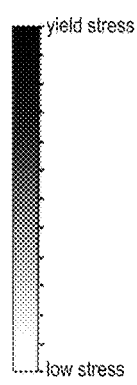
*FIG. 4A*  *FIG. 4B*

APPARATUSES AND METHODS FOR ENDOSCOPIC TOOL JOINTS

BACKGROUND

Technical Field

The present disclosure generally relates to endoscopic tools and methods of use. More particularly, and without limitation, the disclosed embodiments relate to apparatuses, devices, and methods for a joint to secure two tubular components of an endoscopic tool.

Background Description

Endoscopic procedures often require the introduction of a tool through the internal working lumen of an endoscope. For example, in an endoscopic ultrasound (EUS) procedure, a fine needle aspiration (FNA) needle or a fine needle biopsy (FNB) needle is often introduced through the working lumen for delivery to the distal tip of the endoscope. Under ultrasonic guidance, the needle is used to collect tissue samples for subsequent examination and testing.

Endoscopic needles often consist of a long body, with a sharp tip at the distal end and a handle at the proximal end. They are often constructed of stainless steel because it is low-cost, has sufficient column strength for endoscopic procedures, and is sufficiently flexible in most situations. However, stainless steel plastically deforms when inserted through a tortuous path or when used multiple times, such as during multiple biopsy runs during a single procedure. Typically, when a stainless steel needle is inserted through the bending section and over the elevator of an EUS endoscope, the needle emerges from the distal end of the endoscope plastically deformed and potentially damaged. This deformation is permanent and is the result of the stainless steel being subjected to stress beyond its elastic limit.

There are numerous disadvantages to performance of an endoscopic procedure with a deformed or damaged needle. For example, during an EUS procedure, a bent needle may bend out of the two-dimensional viewing plane of the ultrasonic sensor. The needle is thus undetectable and is difficult to track and guide during sampling. Additionally, it is challenging to steer a bent needle because it will arc away from the intended path of movement. This may result in difficulties in biopsying the intended tissue site, extended procedure time, physician fatigue, and could result in patient harm. Further, a stylet may become stuck in a bent needle, or a physician may find it difficult to introduce a stylet through a bent needle.

Other prior endoscopic needles have been constructed of nitinol. Nitinol is superelastic and provides superior flexibility to stainless steel while still maintaining column strength and tensile strength for needle insertion and retraction. Superelastic nitinol needles can be introduced through the extreme bends of an endoscopic bending section and elevator and still return to a straight position after. However, nitinol is cost-prohibitive, especially considering the large amounts required to construct a single endoscopic needle. A nitinol endoscopic needle between six and seven feet in length may cost a hospital or healthcare provider twice as much as a stainless steel endoscopic needle of the same length. A significant number of hospitals and healthcare providers are unwilling or unable to afford the additional cost for nitinol endoscopic needles.

Therefore, an improved endoscopic needle is needed that provides the same flexibility and strength of nitinol needles with significantly reduced cost. Such an improved needle may address the deformation problems faced by stainless steel endoscopic needles and may also be more cost-effective than nitinol endoscopic needles.

SUMMARY

The embodiments of the present disclosure include apparatuses, systems, and methods for tools adapted for insertion into the body of a patient. Advantageously, the exemplary embodiments provide a tool constructed of a first tube secured to a second tube with an adhesive or solder window arrangement.

According to an exemplary embodiment of the present disclosure, a tool adapted for insertion into a body of a patient is described. The tool includes a first tube and a second tube. The second tube includes one or more windows in a proximal portion thereof. A distal portion of the first tube is positioned within the proximal portion of the second tube such that each of the windows overlays the distal portion of the first tube. Each of the windows is at least partially filled with adhesive or solder such that the first tube is secured to the second tube.

According to a further exemplary embodiment of the present disclosure, a method of manufacturing a tool adapted for insertion into a body of a patient is described. The method includes providing a first tube and providing a second tube. The second tube includes one or more windows in a proximal portion thereof. The method further includes inserting a distal portion of the first tube within the proximal portion of the second tube such that each of the one or more windows overlays the distal portion of the first tube. The method further includes at least partially filling each of the one or more windows with adhesive or solder such that the first tube is secured to the second tube.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 4A is a side plan view of stresses on an exemplary nitinol tube with windows spanning 44% of its outer circumference during FEA simulations in an example according to the present disclosure.

FIG. 4B is a side plan view of stresses on a comparison nitinol tube with windows spanning 88% of its outer circumference during the FEA simulations in the example of FIG. 4A.

DETAILED DESCRIPTION

Figure 1:
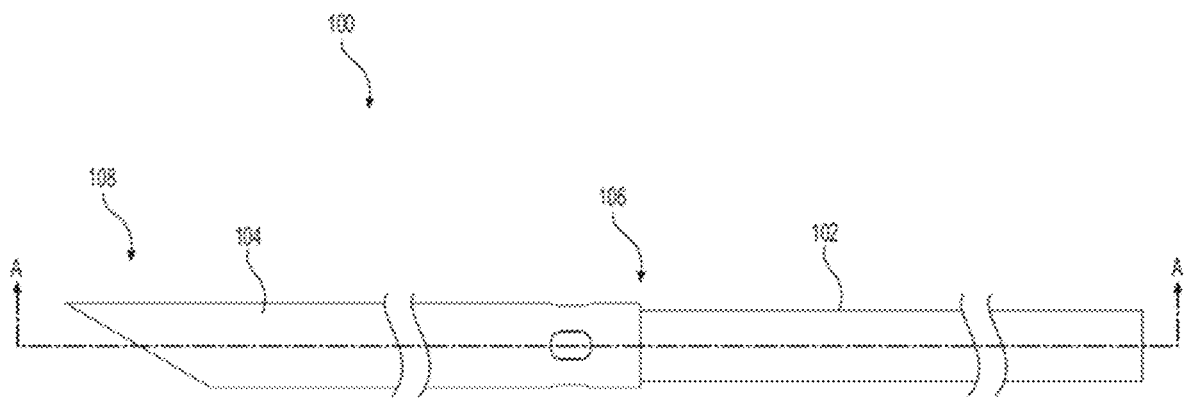
FIG. 1 is a side plan view of an exemplary body-inserted tool, according to embodiments of the present disclosure.

The disclosed embodiments relate to systems, apparatuses, and methods for improved body-inserted tools. Embodiments of the present disclosure may be implemented with endoscopic needles for performing suitable diagnostic and/or therapeutic operations, such as FNA needles or FNB needles. However, it will be appreciated that embodiments of the present disclosure are not limited to endoscopic needles, and that the systems, apparatuses, and methods disclosed herein may be implemented with any suitable body-inserted tool or with any suitable tubular structure.

As described herein, an endoscope typically includes a proximal end and a distal end. A proximal end may refer to a point or a location along the length of the endoscope closer to a physician or a medical practitioner. A distal end may refer to a point or location along the length of the endoscope closer to a diagnosis or treatment site in the body of a patient during an endoscopic procedure. As described herein, the longitudinal axis of a given channel or tubular structure may refer to a central axis or an off-center axis of the channel or tubular structure.

An endoscope often includes one or more internal lumens extending between the distal end and the proximal end. One of the internal lumens may serve as a working channel to introduce an endoscopic tool to a desired diagnosis or treatment site at the distal end of the endoscope. An endoscope may additionally include a bending section and elevator near the distal end, both of which may have at least one extreme bend. The working channel extends through the bending section and the elevator; as a result, when an endoscopic tool is introduced through the working channel, it must pass through the extreme bends of these sections.

Endoscopic tools, such as endoscopic needles, are often constructed of stainless steel. Stainless steel tools are cost effective but do not provide the elastic flexibility necessary for passing through the bending section without being damaged. Nitinol tools provide the necessary elastic flexibility but can be prohibitively expensive for many hospitals to use on a regular basis. Various embodiments of the present disclosure describe a hybrid endoscopic tool, wherein the shaft is constructed of stainless steel hypodermic tubing and the distal end of the tool is constructed of nitinol. This allows for the tool to be extremely flexible where it is needed (e.g. the distal end within the endoscope bending section and the elevator) but also minimize cost by using considerably less nitinol than a full-length nitinol tool. Various embodiments of the present disclosure describe a novel joint for securing the stainless steel tubing and the nitinol tubing together, allowing sustained use of the tool in endoscopic procedures without breakage of the joint.

Reference will now be made in detail to embodiments and aspects of the present disclosure, examples of which are illustrated in the accompanying drawings. Where possible, the same reference numbers will be used throughout the drawings to refer to the same or like parts.

FIG. 1 is a side plan view of an exemplary body-inserted tool 100. In some embodiments, tool 100 may be a needle with a needle tip 108 at a distal end thereof. Tool 100 may include first tube 102 and second tube 104. First tube 102 may extend from the proximal end of tool 100. In some embodiments, the proximal end of first tube 102 may be connected to a handle which a physician may operate to control tool 100. Second tube 104 may extend to the distal end of tool 100. In some embodiments, the distal end of second tube 104 may be sharpened into a needle tip using known methods such as grinding and/or laser cutting. In some embodiments, the needle tip of tool 100 may be used for one or more of punctures of a tissue site and collecting a tissue sample.

A distal portion of first tube 102 may be inserted into a proximal portion of second tube 104 and secured relative to it according to various embodiments explained below. This overlap may form joint 106. In some embodiments, first tube 102 may be constructed of stainless steel. In some embodiments, second tube 104 may be constructed of a metal alloy of nickel and titanium, such as nitinol. First tube 102 may be longer than second tube 104. As a result, joint 106 may be positioned in closer proximity to the distal end of tool 100 than to the proximal end of tool 100. First tube 102 may be between 24 inch and 72 inches in length. In some embodiments, second tube 104 may be between 4 inches and 12 inches in length. In some alternative embodiments in which tool 100 is positioned within the working channel of an endoscope, second tube 104 may have a longitudinal length which is slightly longer than the longitudinal length of the bending section. First tube 102 may have a hypodermic tubing gauge of between 16 and 27. Second tube 104 may have a hypodermic tubing gauge of between 15 and 26. First tube 102 and second tube 104 may be sufficiently similar in diameter such that a small gap extends between them in the overlapping section thereof. According to embodiments in which tool 100 is an endoscopic tool, first tube 102 and second tube 104 may have diameters which are sufficiently small to provide the necessary flexibility for endoscopic procedures.

In some embodiments, tool 100 may be configured for introduction into and use within the working channel of an endoscope, such as an EUS endoscope. Tool 100 may be configured such that when it is positioned within the working channel within the body of the endoscope shaft, second tube 104 is also position in the working channel but lies within the bending section and elevator of the endoscope. Joint 106 may be positioned immediately proximal to the proximal end of the bending section, and first tube 102 may extend proximally beyond the biopsy port of the endoscope. Because nitinol is superelastic, second tube 104 is not plastically deformed or damaged by placement within the bending section and elevator. As a result, second tube 104 may be straight and undamaged when it is extended distally beyond the tip of the endoscope. According to embodiments in which the distal end of second tube 104 includes a needle tip, the needle tip may be straight and undamaged when extended distally beyond the tip of the endoscope. First tube 102 is also not deformed or damaged during introduction of tool 100 into the working channel because the stainless steel from which first tube 102 is constructed is sufficiently flexible to withstand the bends through which first tube 102 is passed. First tube 102 may be passed through a portion of the endoscope shaft with less severe bends than the elevator and bending section of the endoscope.

Tool 100 may constitute an improvement over prior body-inserted tools, such as prior needles, because no portion thereof is damaged during introduction into or use within the working channel of the endoscope. First tube 102 and second tube 104 may provide the necessary column strength and tensile strength for performance of endoscopic procedures using tool 100, especially when they are connected at joint 106 according to various embodiments explained below. As a result, tool 100 may be utilized to perform endoscopic procedures without being deformed or damaged, as many prior tools are. Additionally, tool 100 may constitute an improvement over prior tools constructed solely of nitinol because the majority of the body of tool 100 may be constructed of stainless steel, which is significantly less expensive than nitinol. As a result, tool 100 may cost significantly less than prior nitinol tools when both the raw materials and the manufacturing are considered.

Figure 2A:
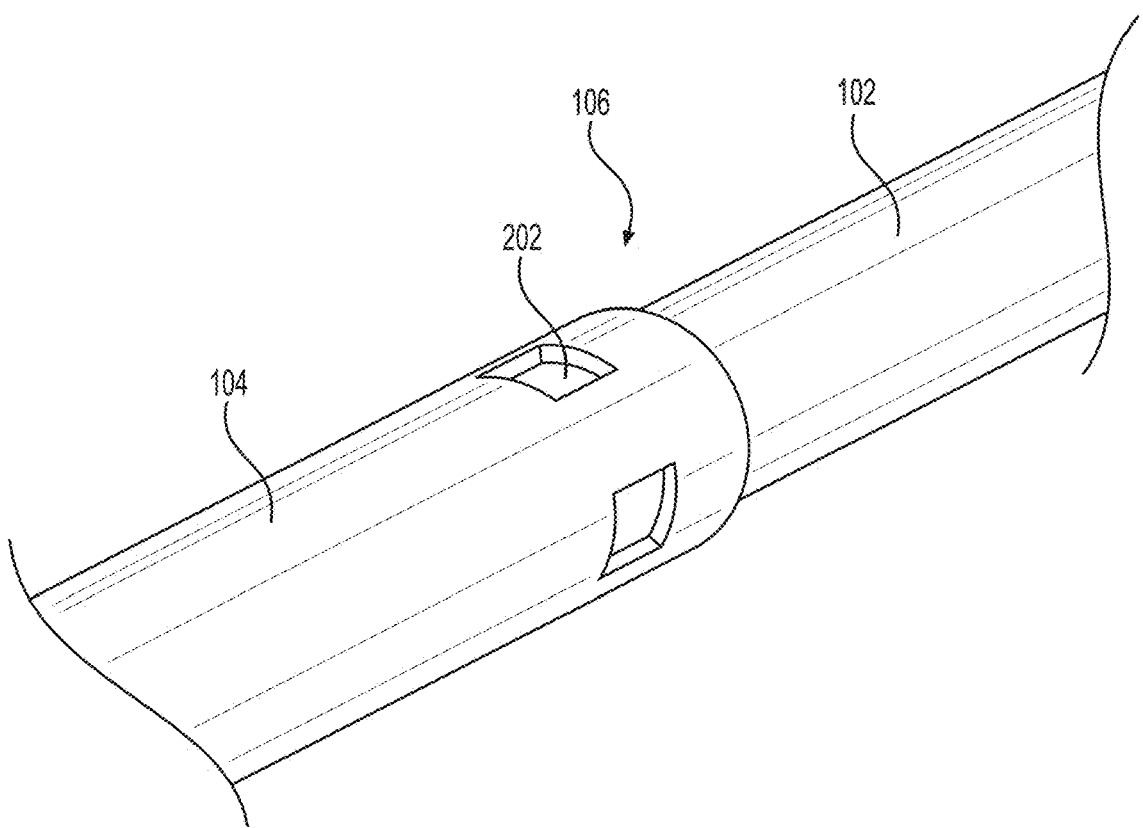
FIG. 2A is a partial perspective view an exemplary body-inserted tool, according to embodiments of the present disclosure.

FIG. 2A is a partial perspective view an exemplary body-inserted tool 100. Second tube 104 may include one or more windows 202 in a proximal portion thereof. When first tube 102 is inserted within second tube 104, windows 202 may overlap first tube 102 such that the distal end of first tube 102 is positioned distally of windows 202. Joint 106 may be formed by the insertion of first tube 102 into second tube 104 and the at least partially filling of windows 202 with adhesive or solder. The adhesive or solder may secure first tube 102 and second tube 104 together such that joint 106 may withstand considerable forces, including those far greater in magnitude than typically experienced by body-inserted tools.

Figure 2B:
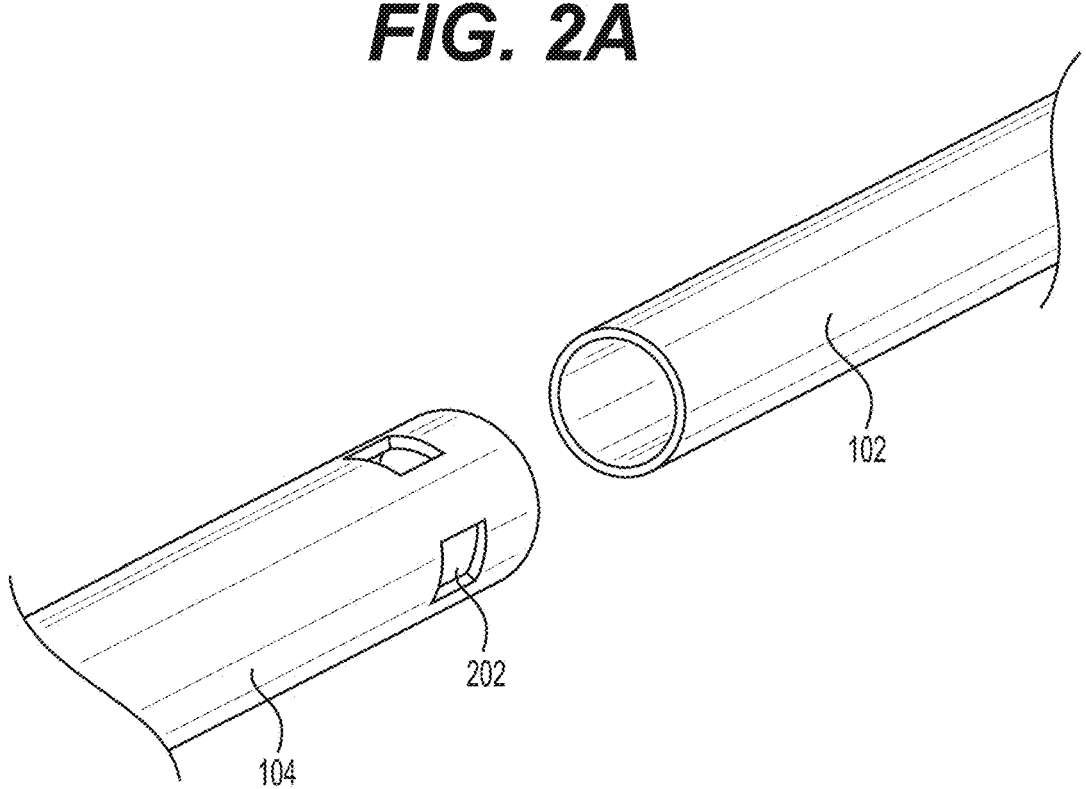
FIG. 2B is a partial component view of the exemplary body-inserted tool of FIG. 2A, according to embodiments of the present disclosure.

FIG. 2B is a partial component view of exemplary body-inserted tool 100. In some embodiments, the one or more windows 202 includes a single window. In some alternative embodiments, the one or more windows 202 includes a plurality of windows. In some embodiments, windows 202 may include a plurality of windows which are evenly spaced along a circumference of second tube 104. In some alternative embodiments, windows 202 may include a plurality of windows spaced at irregular intervals along a circumference of second tube 104. In some further alternative embodiments, windows 202 may be spaced at multiple longitudinal positions along the length of second tube 104. Each window of windows 202 may be positioned a distance of between 0.015 inches and 0.200 inches away from a proximal end of second tube 104.

Windows 202 may be laser cut in second tube 104. Alternatively, windows 202 may be formed using other techniques. Windows 202 may be sufficiently large enough receive deposits of adhesive or solder. Windows 202 may be rectangular, square-shaped, circular, or polygonal. In some embodiments, windows 202 may be rectangular, with a longer dimension extending in a direction parallel to the longitudinal axis of second tube 104. In some embodiments, the corners of windows 202 may be curved due to the formation of windows 202 with laser cutting. Windows 202 may be cut radially into second tube 104 such that a width of windows 202 along the outer diameter of second tube 104 may be slightly larger than a width of windows 202 along the inner diameter of second tube 104. Each window of windows 202 may have an arc length of between 22.5° and 270° about the circumference of second tube 104. In embodiments in which windows 202 includes a plurality of windows, a total additive arc length of the plurality of windows may constitute 25% to 75% of one or both of the inner circumference and the outer circumference of second tube 104. That is, when the arc lengths of each individual window are summed to produce an aggregate arc length, that aggregate arc length may constitute 25% to 75% of one or both of the inner circumference and the outer circumference of second tube 104. Second tube 104 may have a diameter large enough to permit the at least one window 202 to be large enough to receive adhesive or solder therein. Additionally, second tube 104 may provide sufficient nitinol between each window so that forces generated during use of tool 100 do not cause fracturing of the inter-window nitinol or of joint 106. Each window of windows 202 may have a longitudinal length of between 0.015 inches and 0.150 inches.

Figure 2C:
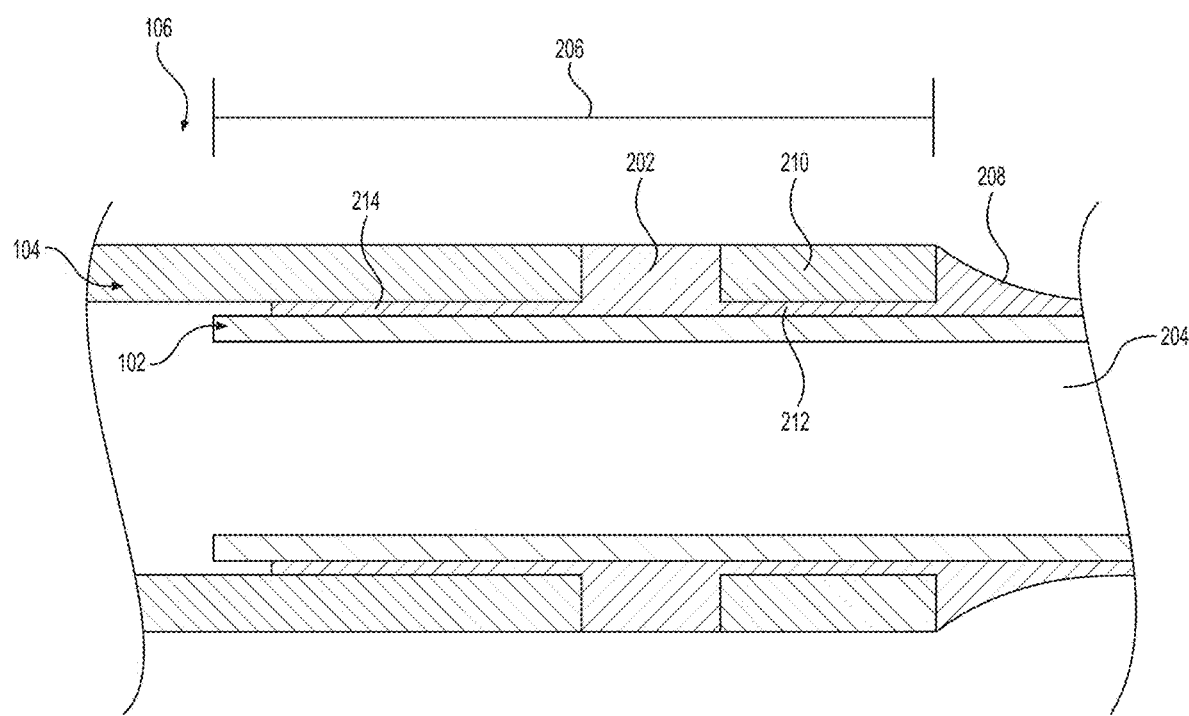
FIG. 2C is a partial cross-sectional view of the exemplary body-inserted tool of FIG. 2A, according to embodiments of the present disclosure.

FIG. 2C is a partial cross-sectional view of exemplary body-inserted tool 100. First tube 102 may be at least partially inserted within second tube 104 so as to form overlapping section 206. Tool lumen 204 may extend through both tubes. After first tube 102 and second tube 104 are positioned relative to each other, adhesive or solder may be back-filled within windows 202 to secure the tubes together. An exemplary adhesive may include, and is not limited to, cyanoacrylate, UV cured adhesives or structural epoxies. An exemplary solder may include, and is not limited to, tin-silver alloy, tin-lead, tin-zinc, lead-silver, zinc-aluminum, gold alloy, or tin-bismuth. Flux may additionally be used in some embodiments. An exemplary flux may include, and is not limited to, acid-based fluxes and chloride-based solders. During back-filling of windows 202, adhesive or solder may be allowed to wick along the space between first tube 102 and second tube 104. For example, adhesive or solder may wick into space 214 distal of the windows 202 and/or into space 212 between windows 202 and the proximal end 210 of the second tube. Alternatively or additionally, adhesive or solder may be placed at the proximal end 210 of the second tube to form a fillet 208. Fillet 208 may touch the outer surface of first tube 102, thus further securing the tubes together. During formation of fillet 208, adhesive or solder may be allowed to wick along space 212. In some embodiments, adhesive or solder may be back-filled within windows 202 until the adhesive or solder reaches the outer diameter of second tube 104. The adhesive or solder deposits within windows 202 may form a smooth surface with second tube 104.

In some embodiments, fillet 208 may be formed prior to delivery of adhesive or solder to windows 202. In some alternative embodiments, windows 202 may be at least partially back-filled with solder or adhesive prior to formation of fillet 208. Fillet 208 may extend along the entire circumferential length of first tube 102. Prior to soldering or delivery of adhesive, first tube 102 and second tube 104 may be cleaned using known methods, such as chemical or mechanical cleaning methods. In some embodiments, flux may be used as a striping agent after use of a chemical etching treatment. The length of overlapping section 206 between first tube 102 and second tube 104 is sufficiently long such that solder or adhesive does not wick into the lumen of either tube. The length of overlapping section 206 is sufficiently short such that joint 106 is sufficiently pliable for endoscopic use. In some embodiments, overlapping section 206 is between 0.040 inches and 0.250 inches in length.

Back-filling of adhesive or solder within windows 202 may produce a stronger bond between the tubes than adhering or soldering two tubes without windows. When the adhesive or solder hardens within windows 202, it may form hard blocks, or "Frankenstein bolts," which are secured to first tube 102 and which are retained within the windows. This may be due, at least in part, to the strong bond between stainless steel and adhesive or solder. As a result, second tube 104 cannot be moved longitudinally or rotationally relative to first tube 102 because second tube 104 cannot be pulled over the Frankenstein bolts. The Frankenstein bolts form a mechanical lock between first tube 102 and second tube 104 even in the event that the adhesive or solder does not bond to the nitinol of second tube 104 because the pins cannot be pulled out from the windows 202. In some embodiments, the tubes may be separated only if the solder or adhesive is sheared off of first tube 102.

Figure 3A:
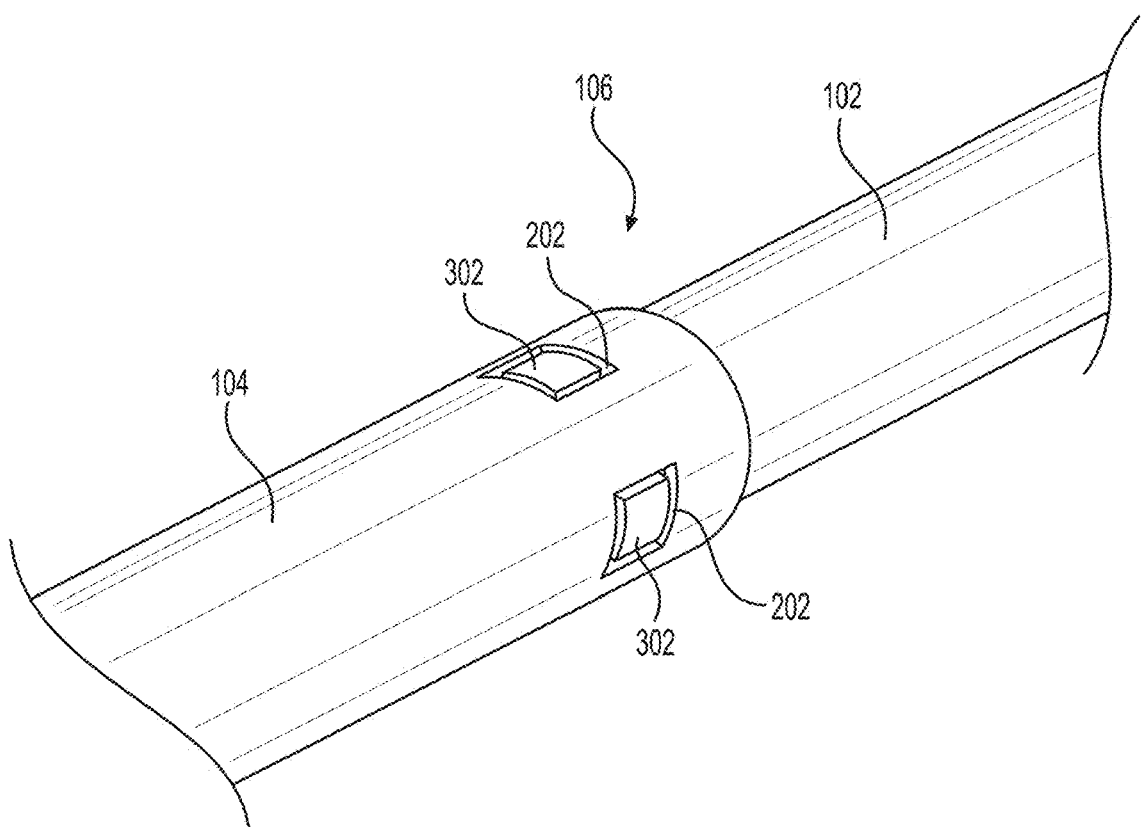
FIG. 3A is a partial perspective view an exemplary body-inserted tool including exemplary blocks, according to embodiments of the present disclosure.

FIG. 3A is a partial perspective view an exemplary body-inserted tool 100. Tool 100 may include blocks 302 positioned within one or more of windows 202. Blocks 302 may be rectangular, square-shaped, circular, or polygonal. Blocks 302 may have the same shape as windows 202. In some embodiments, blocks 302 may be sized to be positioned within windows 202, with a small margin extending around the sides of each block 302. Optionally, the margin may then be filled with adhesive or solder. In some alternative embodiments, blocks 302 may be sized to fill the entire volume of the windows 202 such that the margin around the blocks is eliminated. In some embodiments, the outer surfaces of blocks 302 may be even with the outer surface of second tube 104 when blocks 302 are positioned within windows 202. In some alternative embodiments, the outer surfaces of blocks 302 may be positioned radially inwards from the outer surface of second tube 104, and the outer surfaces of blocks 302 may be covered with adhesive or solder.

Figure 3B:
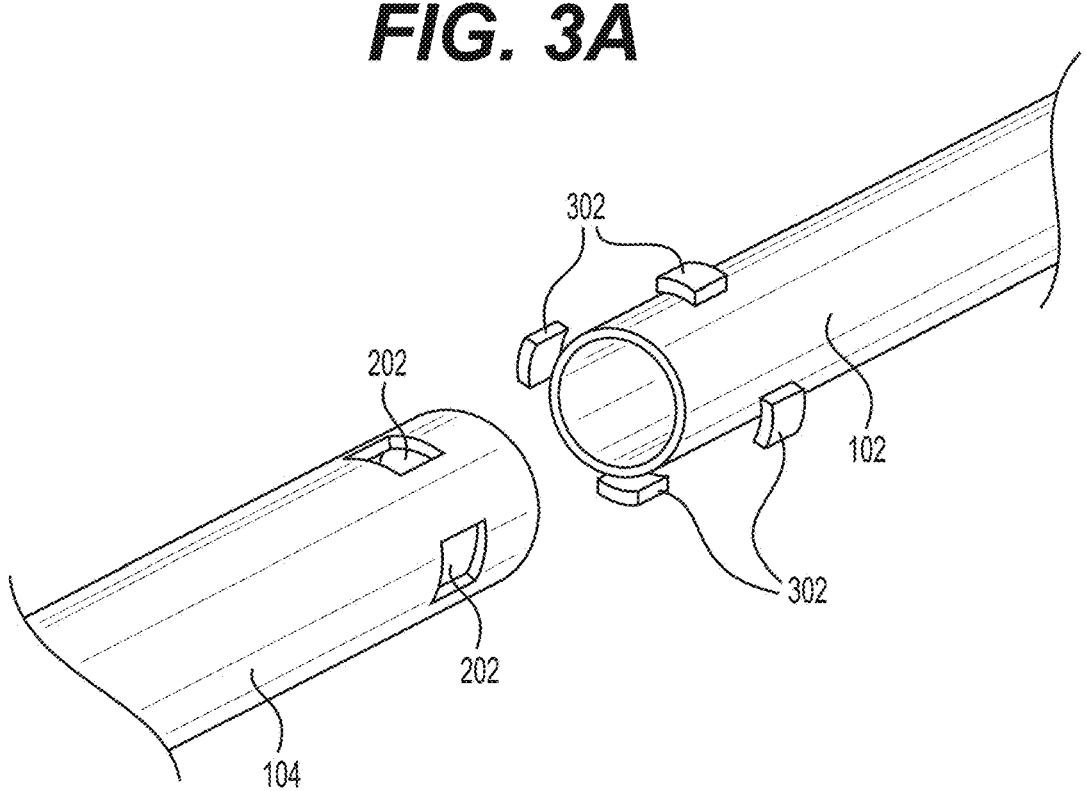
FIG. 3B is a partial component view of the exemplary body-inserted tool of FIG. 3A, according to embodiments of the present disclosure.

FIG. 3B is a partial component view of exemplary body-inserted tool 100 with exemplary blocks 302. In some embodiments, first tube 102 may be inserted into distal tube 104, after which blocks 302 may be inserted into windows 202 and secured to first tube 102. Blocks 302 may be secured to first tube 102 using known methods, such as laser welding or resistance welding. According to embodiments in which a margin extends around blocks 302, the margin may be back-filled with adhesive or solder. In some embodiments, fillet 208 may be formed before, during, or after placement of blocks 302 within windows 202. Adhesive or solder may be allowed to wick into one or more of space 212 and space 214 during one or more of window back-filling and fillet 208 formation. In some embodiments, blocks 302 may be constructed of the same material as first tube 102, such as stainless steel.

Figure 3C:
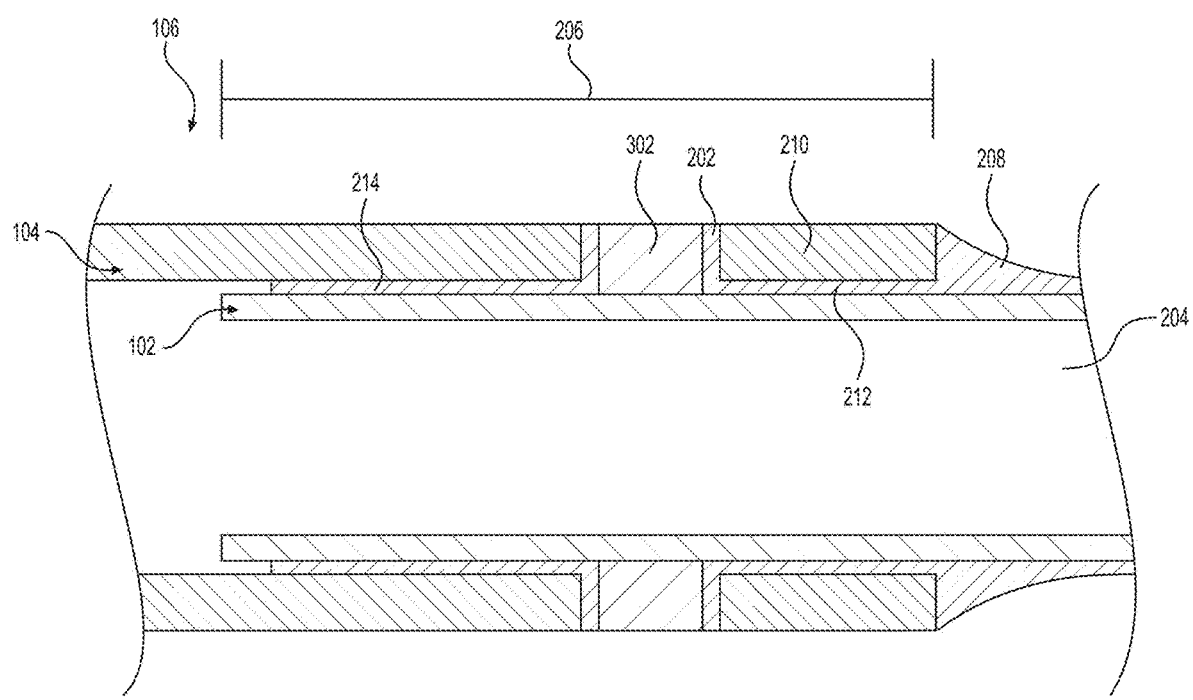
FIG. 3C is a partial cross-sectional view of the exemplary body-inserted tool of FIG. 3A, according to embodiments of the present disclosure.

FIG. 3C is a partial cross-sectional view of exemplary body-inserted tool 100 with exemplary blocks 302. Joint 106 with blocks 302 may provide a more secure connection between first tube 102 and second tube 104 than prior joints formed by soldering two cylindrical tubes without windows. First tube 102 and second tube 104 may be secured against relative rotational and longitudinal movement by blocks 302. In some embodiments, blocks 302 may sit flush with the edges of windows 202, such that relative longitudinal or rotation movement between them is prevented. In some alternative embodiments, blocks 302 may have plugs of adhesive or solder surrounding them, which may fill the margins between blocks 302 and the edges of the windows 202. The filling of the margins may prevent any longitudinal or rotational movement between first tube 102 and second tube 104. The joint may be additionally strengthened by fillet 208 and/or by adhesive or solder wicking between the tubes in overlapping section 206. Because blocks 302 are secured to first tube 102 (for example, by laser welding or resistance welding), they may lock first tube 102 and second tube 104 together because blocks 302 are retained within windows 202. Additionally, in some embodiments, plugs of solder or adhesive surrounding blocks 302 are bonded to blocks 302, first tube 102, and/or second tube 104. This may additionally strengthen the joint between the tubes and blocks 302, and may provide hard plugs (Frankenstein bolts) that are retained within windows 202. Even in the event that the adhesive or solder does not bond to the nitinol of second tube 104, the joint between the tubes will be strong due to blocks 302 and the Frankenstein bolts of adhesive or solder.

Tools formed with exemplary joints of the present disclosure may provide a number of benefits over prior tools, including prior endoscopic needles constructed solely of stainless steel or solely of nitinol. In some embodiments, the nitinol second tube 104 may provide enhanced flexibility, thus preventing deformation or destruction of the tool. Additionally, exemplary tools are significantly less expensive than prior tools constructed solely of nitinol due to the fact that large portions of the exemplary tools are constructed of stainless steel. Further, exemplary joints 106 provide a much stronger connection between first tube 102 and second tube 104 than prior joints formed by soldering two tubes without windows. This may be due, at least in part, to the presence of adhesive or solder pins within windows 202, and optionally of blocks 302, which may be positioned within windows 202 and secured to first tube 102. Exemplary tools of the present disclosure may be significantly less expensive than prior nitinol tools, and may provide the necessary column strength and joint strength to perform endoscopic procedures without sustaining damage to any portion thereof.

EXAMPLES

1. Tubes Connected with Solder-Filled Windows Failed at Higher Pull Forces than Soldered Tubes without Windows According to an example, exemplary tools with solder-filled windows were subjected to pull tests until failure of the joint between the nitinol tube and the stainless steel tube. Each tool was constructed of a 19 gauge nitinol tube and a 20 gauge stainless steel tube. The nitinol tubes were chemically etched to remove the oxide layer and Indalloy #121 solder and Indium #2 flux were used to join the stainless steel and nitinol tubes. The nitinol tube included four circumferentially spaced windows, each of which was filled with solder to join the nitinol tube to the stainless steel tube according to embodiments of the present disclosure. A tensile testing unit was utilized to subject the tools to straight pull until failure. Both ends of the tools were clamped during testing. Mandrels were inserted into the open ends of each tool to prevent the clamps from crushing the tubing.

For comparison, a group of control tubes of the same hypodermic gauges were also subjected to the same pull test until failure of the joint between the nitinol tube and the stainless steel tube. The control tubes were constructed of a stainless steel tube inserted within and soldered to a nitinol tube, which did not have windows. The nitinol control tubes were chemically etched to remove the oxide layer and Indalloy #121 solder and Indium #2 flux were used to join the stainless steel and nitinol tubes.

Table 1 below recites the data for the pull test for the tools with solder-filled windows.

TABLE 1

| Sample | Axial Force at Failure (lbf) |
| --- | --- |
| 1 | 28.98 |
| 2 | 45.94 |
| 3 | 37.86 |
| 4 | 55.80 |
| 5 | 55.79 |
| 6 | 56.95 |
| 7 | 55.76 |
| 8 | 56.87 |
| 9 | 47.80 |
| 10 | 57.27 |
| 11 | 55.68 |
| 12 | 55.82 |
| 13 | 55.98 |
| 14 | 53.95 |
| 15 | 55.93 |

Table 2 below recites the data for the pull test for the control group.

TABLE 2

| Sample | Axial Force at Failure (lbf) |
| --- | --- |
| 1 | 33.15 |
| 2 | 32.41 |
| 3 | 33.71 |
| 4 | 31.74 |
| 5 | 33.50 |
| 6 | 35.16 |

The tools with solder-filled windows according to the present disclosure failed at an average force of 51.76 lbf, with a standard deviation of 8.30 lbf. In comparison, the control group failed at an average force of 33.28 lbf, with a standard deviation of 1.18 lbf. These findings demonstrate that exemplary joints formed with solder-filled windows may provide a stronger connection between the tubes than does soldering the tubes without windows, regardless of the technique utilized to manufacture the tube without windows. This suggests that tools constructed with solder-filled windows may be better suited for clinical procedures, as they may be subjected to higher forces without breakage of the joint.

2. FEA Simulation of Different Sized Windows Indicates Yield Stresses in Windows Spanning 88% of the outer Circumference of the Nitinol Tube According to another example, an exemplary tool of the present disclosure was subjected to FEA (fine element analysis) simulations using SolidWorks software. In these simulations, the nitinol tube included four windows and was fixed at the distal end. The total additive arc length of the plurality of windows constituted 44% of the outer circumference of the nitinol tube. The stainless steel tube had a pin within each of the windows to secure the tubes together. The opposite end of the stainless steel tube was subjected to 30 pounds of tensile force on an inner piece. Stresses on the nitinol tube were simulated.

To evaluate the effect of enlarging the windows, a comparison tool was simulated with identical specifications as the first tool except the total additive arc length of the plurality of windows constituted 88% of the outer circumference of the nitinol tube. This comparison tool was subjected to the same 30 pounds of tensile force.

FIG. 4A depicts stresses on the exemplary nitinol tube with windows constituting 44% of its outer circumference. The tube experienced localized stress at the corners of each window. However, no portion of the exemplary nitinol tube reached yield stress during testing.

FIG. 4B depicts stresses on the comparison nitinol tube with windows constituting 88% of its outer circumference. The comparison tube experienced higher stresses than the exemplary tube, with yield stress being reached in the struts between the windows. These findings suggest that tubes with very large windows and small struts between them may be susceptible to yield stress and failure at the site of the small struts. These findings also suggest that the exemplary nitinol tube may be better suited for endoscopic procedures than the comparison tube with larger windows because the comparison tube may experience yield stress at a lower applied force.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A tool adapted for insertion into a body of a patient, the tool comprising:

a first tube; and a second tube comprising one or more windows in a proximal portion thereof, wherein a distal portion of the first tube is positioned within the proximal portion of the second tube such that each of the windows overlays the distal portion of the first tube, and wherein each of the windows is filled with at least one of adhesive or solder such that the first tube is fixedly secured to the second tube.

2. The tool of claim 1, wherein the first tube is constructed of stainless steel.

3. The tool of claim 1, wherein the second tube is constructed of nitinol.

4. The tool of claim 1, wherein the second tube comprises a plurality of windows.

5. The tool of claim 4, wherein a total additive arc length of the plurality of windows constitutes 25%-75% of the outer circumference of the second tube.

6. The tool of claim 1, wherein the one or more windows are rectangular.

7. The tool of claim 1, wherein the one or more windows each have an axial length of between 0.015 inches and 0.150 inches.

8. The tool of claim 1, wherein at least one of adhesive or solder extends between the first tube and the second tube along the length of an overlapping portion of the first tube and the second tube.

9. The tool of claim 8, wherein the length of the overlapping portion is between 0.040 inches and 0.250 inches.

10. The tool of claim 1, wherein the one or more windows are positioned a distance of between 0.015 inches and 0.200 inches away from a proximal end of the second tube.

11. The tool of claim 1, further comprising
one or more blocks, wherein each of the blocks is positioned within a corresponding one of the one or more windows and is welded to the first tube.

12. The tool of claim 11, wherein the one or more blocks are constructed of stainless steel.

13. The tool of claim 11, wherein an area within each of the one or more windows surrounding the corresponding block is filled with at least one of adhesive or solder.

14. The tool of claim 1, wherein the at least one of adhesive or solder within each of the one or more windows extends to an outer diameter of the second tube.

15. The tool of claim 1, wherein a distal end of the second tube comprises a needle tip.

16. The tool of claim 1, wherein a proximal end of the second tube forms a joint with the first tube, the joint being covered with solder.

17. The tool of claim 1, wherein the first tube and the second tube each have inner diameters of between 0.00825 inches and 0.047 inches.

* * * * *